(12) United States Patent
Pop et al.

(10) Patent No.: US 8,804,897 B2
(45) Date of Patent: Aug. 12, 2014

(54) INTEGRATED METHOD TO ANALYZE CRYSTALS IN DEPOSITS

(75) Inventors: Mihai G. M. Pop, Lynchburg, VA (US); Brian Glenn Lockamon, Evington, VA (US); Vladimir Oleshko, Phoenix, AZ (US); James Howe, Earlysville, VA (US)

(73) Assignee: AREVA Inc., Lynchburg, VA (US)

( * ) Notice: Subject to any disclaimer, the term of this patent is extended or adjusted under 35 U.S.C. 154(b) by 2098 days.

(21) Appl. No.: 11/490,952

(22) Filed: Jul. 21, 2006

(65) Prior Publication Data

US 2014/0183356 A1    Jul. 3, 2014

(51) Int. Cl.
    G21C 9/00      (2006.01)
    G21C 17/022    (2006.01)

(52) U.S. Cl.
    CPC ....... *G21C 17/0225* (2013.01); *G21Y 2002/103* (2013.01)
    USPC .......................................................... 376/305

(58) Field of Classification Search
    CPC ...................... G21C 17/0225; G21Y 2002/103
    USPC .......................................................... 376/305
    See application file for complete search history.

(56) References Cited

U.S. PATENT DOCUMENTS

| | | | |
|---|---|---|---|
| 4,233,509 A | 11/1980 | Tamura et al. | |
| 4,483,205 A | 11/1984 | Bellaiche et al. | |
| 4,717,826 A | 1/1988 | Silver | |
| 5,023,453 A | 6/1991 | Adachi et al. | |
| 5,089,699 A | 2/1992 | Ose et al. | |
| 5,446,798 A | 8/1995 | Morita et al. | |
| 5,779,814 A | 7/1998 | Fellers et al. | |
| 5,869,833 A | 2/1999 | Richardson et al. | |
| 5,950,192 A | 9/1999 | Moore et al. | |
| 6,370,479 B1 | 4/2002 | Tomikawa et al. | |
| 6,466,637 B2 | 10/2002 | Bowen et al. | |
| 6,664,552 B2 | 12/2003 | Shichi et al. | |
| 6,680,206 B1 | 1/2004 | McDevitt et al. | |
| 6,683,305 B1 | 1/2004 | Lu et al. | |
| 6,748,345 B2 | 6/2004 | Chou et al. | |
| 6,765,205 B2 | 7/2004 | Ochiai et al. | |
| 6,794,663 B2 | 9/2004 | Shichi et al. | |
| 7,072,103 B1 | 7/2006 | Atchison | |
| 7,091,484 B2 | 8/2006 | Yanagiuchi et al. | |

FOREIGN PATENT DOCUMENTS

| | | |
|---|---|---|
| JP | 2005-114384 A | 4/2005 |
| JP | 2007-533996 A | 11/2007 |
| WO | WO 01/95365 | 12/2001 |
| WO | 2005-101997 A2 | 11/2005 |

OTHER PUBLICATIONS

PCT International Search Report from PCT/US2007/012471, mailed on Aug. 27, 2008.

*Primary Examiner* — Frank J McGue

(74) *Attorney, Agent, or Firm* — Davidson, Davidson & Kappel, LLC

(57) ABSTRACT

A method to analyze crystals in a deposit on a surface of a nuclear generating station heating surface, wherein the method extracts a sample of material from the surface of the nuclear generating station heating surface and also includes conducting at least one of a high resolution scanning electron microscope/energy dispersive X-ray spectrometry of the sample and a scanning transmission electron microscope/selected area electron diffraction/spot and elemental mapping analysis of the sample.

15 Claims, 14 Drawing Sheets

US 8,804,897 B2

INTEGRATED METHOD TO ANALYZE CRYSTALS IN DEPOSITS

FIELD OF THE INVENTION

The present invention relates to the identification of deposit formations. More specifically, the present invention provides an integrated methodology for comprehensive characterization of crystals in deposits encountered in power plants on components such as in nuclear power steam generators and on nuclear fuel.

BACKGROUND INFORMATION

During operation of a nuclear power plant, different materials are deposited upon heating surfaces of the nuclear primary system, thereby causing a change in the heating surface. In most instances, material collects upon the heating surface, thereby causing an insulating effect between the heating surfaces and the coolant of the primary system. In some instances, the material deposited upon the heating surface can cause localized corrosion and/or pitting of the surface.

Operators of nuclear power systems strive to minimize the amount of deposits upon heating surfaces, thereby allowing the best possible performance from reactor systems under controlled conditions. Over time, the deposition of materials upon the heating surfaces can affect the overall economic operability of the nuclear power reactor. In order to increase the economic viability of the nuclear power station, it is desired to ascertain the exact nature of the materials deposited upon the heating surfaces as well as to determine the source of these deposits.

Currently, there is no systematic, well-defined approach to the study of deposits such as nuclear steam generator deposits, or other radioactive crystalline structures in their "as found" condition in irregularities at the surface of the equipment. There is no known way to combine various electron microscopy methods in analytical electron microscopy and/or sample preparation to achieve maximum information about materials such as Chalk River Unidentified Deposits (CRUD), nuclear steam generator deposits or other radioactive deposits to determine these deposits constituents in their "as found" condition for unadulterated portions of the deposits located in irregularities at the surface of the equipment on which they are found.

There is therefore a need to develop a comprehensive method to study deposits, such as nuclear steam generator deposits and CRUD, to determine the deposits crystalline structure.

There is a further need for a method which allows the study of these deposits in an economical and safe manner.

SUMMARY OF THE INVENTION

It is therefore an objective of the present invention to provide an integrated method for comprehensive study of deposits, such as nuclear steam generator deposits or fuel CRUD, to determine the deposits crystalline structure.

It is also a further objective of the present invention to provide a method to study these deposits in an economical and safe manner.

An additional objective of the invention is the adaptation and unique combination of methods of electron microscopy (EM) that comprise high resolution analytical scanning and analytical transmission utilizing multiple imaging modes, as well as selected areas of electron diffraction and energy-dispersive X-ray spectrometry. These methods can be combined to better analyze crystals found mainly in CRUD and steam generator collar deposits, in their "as found" condition, comparing select electron microscopy signals from crystal standards with the signals from the areas of interest, and those of unadulterated portions of the deposits located in irregularities at the surface of deposits under the same radioactive conditions. These methods connect morphological and analytical characterization results with a power diffraction crystal database in order to better understand crystal growth phenomenon in irregularities.

According to the present application, a proposed strategy for characterization of crystals in deposits is provided mainly in nuclear power steam generators and nuclear fuel deposit CRUD flakes for a range of scales varying from 10 to 50 micron size (macrostructural analysis) to 0.1 to 10 micron (microstructural analysis) and down to 0.02 to 400 nanometers (nanostructural analysis).

The present invention provides a method to analyze crystals in a deposit on a surface of a nuclear generating station heating surface that comprises extracting a sample of material from the surface of the nuclear generating station heating surface, conducting at least one of a high resolution scanning electron microscope/energy dispersive X-ray spectrometry of the sample and a scanning transmission electron microscope/selected area electron diffraction/spot and elemental mapping analysis of the sample; then conducting at least one of three-dimensional morphology, surface topography aggregation and determination of flake size/shape, phase separation and chemical composition quantification after the high resolution scanning electron microscope/energy dispersive X-ray spectrometry of the sample; then conducting at least one of an internal structure, morphology and crystal size/shape determination crystallography investigation and a chemical composition investigation after the scanning transmission electron microscope/selected area electron diffraction/spot and elemental mapping analysis of the sample. A Monte Carlo simulation of electron beam-specimen interaction is performed after the at least one of three-dimensional morphology, surface topography aggregation and determination of flake size/shape, phase separation and chemical composition quantification. Results of the high resolution scanning electron microscope/energy dispersive X-ray spectrometry of the sample, the three-dimensional morphology, surface topography aggregation and determination of flake size/shape, phase separation and chemical composition quantification and the Monte Carlo simulation are stored in a structural data base. The results of the internal structure, morphology and crystal size/shape determination, crystallography investigation and the chemical composition investigation are stored in a crystallographic data system.

The method may also be performed such that the Monte Carlo simulation predicts an expected behavior of the sample under specific operating conditions.

The method may also be conducted such that the step of extracting the sample of material from the surface of the nuclear generating station heating surface comprises one of collecting a CRUD sample directly on TEM grids placed on filter paper and placing a sample of standard carbon support film on top of the sample to dislodge a number of crystals from a surface of a flake of the sample of material.

The method may also be performed such that the step of conducting at least one of three-dimensional morphology, surface topography aggregation and determination of flake size/shape, phase separation and chemical composition quantification after the high resolution scanning electron microscope/energy dispersive X-ray spectrometry of the sample is performed by alternating between imaging modes and changing of voltages provided from high 20 to 50 kV to a low of 0.2 to 5 kV to eliminate charging effects resulting from a radioactive field developed during analysis.

The method may further be accomplished, wherein one of the three-dimensional morphology and the phase separation is determined through scanning electron microscope multimode imaging.

The method may also be accomplished wherein a peak-to-background method is used during the step of conducting at least one of a high resolution scanning electron microscope/ energy dispersive X-ray spectrometry of the sample to compensate for geometric effects of the sample surface.

DETAILED DESCRIPTION

Figure 1:
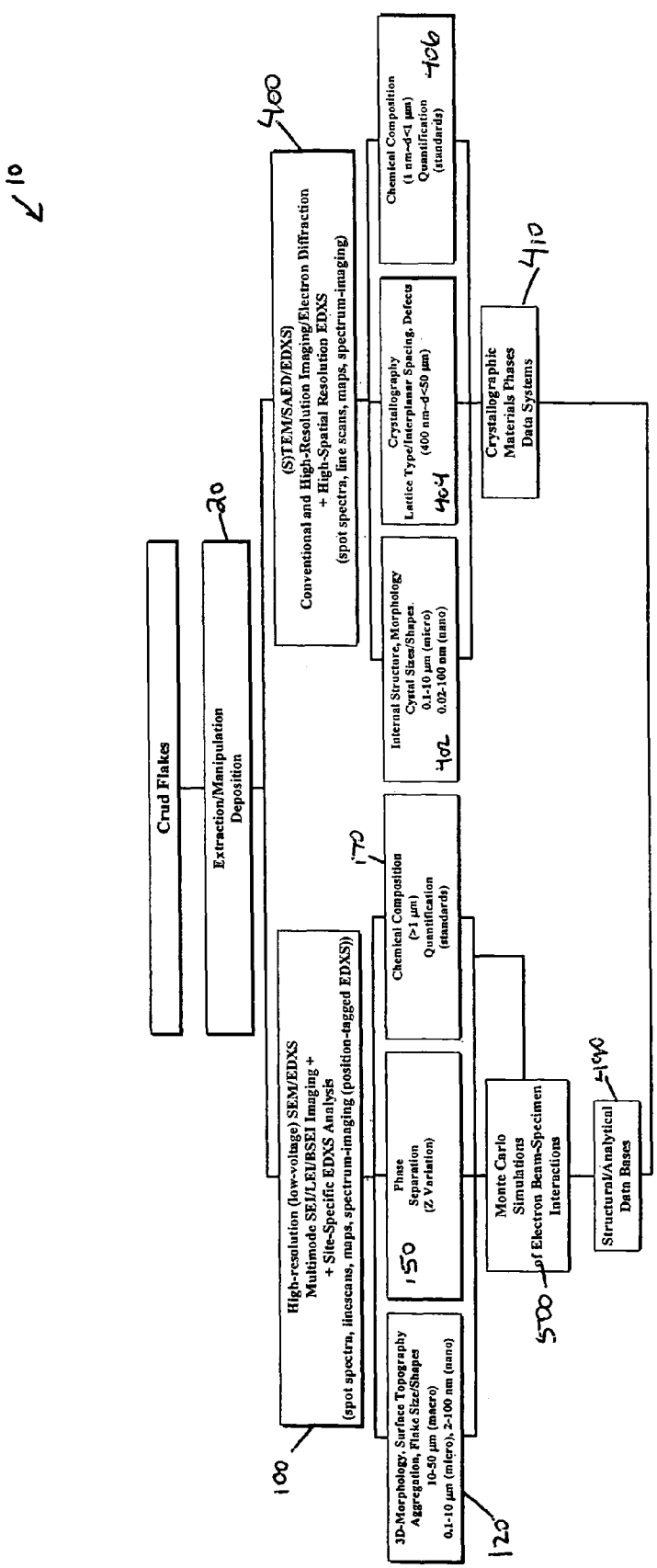
FIG. 1 is a flow chart of a method to analyze crystals in CRUD flake deposits.

The following detailed description is provided in conjunction with the following terms used throughout.

EM—electron microscope: a term used to include all types and configurations of electron microscopes.

SEM—scanning electron microscope (or microscopy): an investigative device used to view minute features of a sample, the device is generally operated at accelerating voltages less than 40 kV. The scanning electron microscope relies on using a small electron probe on the sample surface to produce a signal (image) with the resolution of approximately 1 nm in a field emission scanning electron microscope; the same probe can be used to generate—excite X-rays for energy dispersive X-ray spectrometry of the same regions with approximately 1 μm spatial resolution.

SE—secondary electrons: electrons emitted from the sample surface during evaluation, the electrons have an energy less than 50 eV. The electrons emitted form the SEM images as they are detected by the SEM.

SEI—secondary electron imaging: an image formed from secondary electrons emitted from the sample surface that are used to determine the morphology of a sample provided to an SEM.

BSE—backscattered electrons: incident electrons recoiled/reflected back from the sample by elastic collisions with the atoms.

BSEI—backscattered electron imaging: an image formed from backscattered electrons providing compositional and topographic information.

EBCP—electron backscattered imaging—an image formed from backscattered electrons providing compositional and topographic information.

LEI—lower electron imaging: an image formed from secondary electrons using a lower secondary electron detector (SED) located below the objective lens near the sample plane.

EDXS—energy dispersive X-ray spectrometry: a method of determining the sample composition by analyzing the number of X-rays of characteristic energies emitted from the sample when bombarded by an electron beam.

TEM—transmission electron microscopy (or microscope): A research device generally operated at accelerating voltages >100 kV. The device has the ability to illuminate a wide area of the sample to form an image with resolutions approaching 0.1 nm or focus the probe to obtain EDXS spectra from small areas; it also has the ability to provide electron diffraction data from the same areas.

BF—bright field: an imaging mode in the TEM formed by transmitted electrons.

SAED—selected area electron diffraction: electron diffraction patterns obtained from a limited area of the specimen in TEM using an area-selecting aperture.

EDXS—spot and elemental mapping analyses: X-ray analysis is performed by placing a small stationary probe (spot) on the sample, or by stepping the probe across the sample and obtaining an X-ray analysis at each point to construct a map of the area.

In-chamber ET detector or lower SED: a detector that collects secondary electrons from the point of beam interaction ($SE_1$) and the surrounding area ($SE_2$). It enables a researcher to view the sample from the side, emphasizing peaks and valleys on the sample surface and show fewer effects of charging along the peaks.

Through-the-lens ET detector or upper SED—a detector that collects secondary electrons ($SE_1$) mainly from the surface of the sample. It allows one to view images from above, allowing observation into holes, crevices, irregularities or the topology/morphology of the sample.

STEM—scanning transmission electron microscope: a TEM with a set of coils to scan the focused beam across the specimen as in the SEM and having secondary, backscattered and/or transmitted electron detectors to form the images of the sample.

(S)TEM-scanning transmission electron microscope: an instrument capable of performing as either a TEM or STEM.

FIB—focused ion-beam: a type of microscope like a SEM, but one that accelerates a focused Gallium ion beam onto the specimen instead of an electron beam. The focused beam may be used to mill away the specimen with nanometer resolution and form images from emitted secondary electrons, as in a SEM.

Nano-manipulator systems: mechanical systems such as micro-tweezers that are used to pick up or manipulate submicron features of a specimen.

Compositional (or Compo) mode: refers to images formed from backscattered electrons so that the images obtained correspond to specimen composition (atomic number).

Topographical (or Topo) mode: refers to images formed from backscattered electrons so that the images reflect the specimen topography.

SED—secondary electron detector: a detector used to collect secondary electrons to from an image.

$SE_1$—secondary electrons: secondary electrons emitted from the surface of the sample as a result of primary electron beam—sample interactions. The intensity $I_{SE1}$ of the reflected primary electron beam is proportional to the coefficient of secondary emission and allows the researcher to view images from above, allowing observation into holes, crevices, irregularities or the topology/morphology of the sample.

$SE_2$—secondary electrons: secondary electrons emitted not from the point of beam interaction but from the surrounding area due to higher energy backscattered electrons. The electron intensity $I_{SE2}$ is proportional to the backscattering coefficient η. The $SE_2$ signal is a combination of secondary and backscattered electrons contributing to contrast of the image.

EsB—energy and angle selective backscattered electron detector: a type of integral electron detector that uses a conductive grid to control the energies and angles of secondary and backscattered electrons that the detector collects and uses the controllable mixtures of secondary and backscattered electrons to form an image.

Referring to FIG. 1, a methodology 10 for characterization of crystals of radioactive boiling deposits encountered mainly in nuclear power steam generators and nuclear fuel deposits is presented. The methodology 10 combines electron microscopy methods and methods of preparation for flakes.

In the methodology 10, a first step 20 is the extraction and manipulation of samples from a source. In the present example, techniques from scanning electron microscope (SEM) and scanning transmission electron microscope ((S)TEM) examination of the samples are performed. An extraction and manipulation of the sample entails 1) adhering a sample to be tested to standard carbon SEM stubs using carbon tape. A second alternative extraction technique entails sprinkling a portion of crushed sample onto a standard carbon support film for (S)TEM analyses. The materials provided for the sample may come from scraping and/or other removal methods from the surface to be tested. The samples may be obtained from the heating surfaces of a nuclear system, such as a nuclear steam generator or a nuclear fuel rod.

In the methodology 10, the use of the deposits in their "as found" state is provided. This not only allows for a rapid processing of the deposit (rapid analysis), but also lowers the variability of the results associated with working with crystals in the "as found" state. Alternatively, CRUD flakes, which are composed of a finite number of phases/crystals, are treated such that the identified phases of interest may be chosen to be analyzed. Analyzing the phases of interest by researchers can be performed continuously by repeating the procedure until a desired result (i.e. an observable result for a specified configuration) is achieved.

In the methodology 10, the repeating of the procedure can be performed for a TEM analysis by collecting individual particles on carbon grids for examination in the TEM and/or alternatively (S)TEM. In the TEM, more accurate energy-dispersive X-ray spectrometry EDXS analysis are obtained as the specimens are generally thin. Consequently, probe spreading (a known error causing problem in TEM analysis) is limited and absorption of light elements is reduced. Additionally, selected area electron diffraction (SAED) patterns can be obtained for crystallographic analysis of the phases. For example, phases may be identified by determining their interplanar spacings and comparing these with tabulated values (such as in a crystallographic database) to aid in identification of the crystals present.

In accordance with the present invention, a phase selection process for TEM is a position selective basis process on a CRUD flake using an exact phase selection, e.g., a focused ion beam (FIB) and/or nano-manipulators in the SEM. Samples may also be prepared by collecting CRUD crystals directly up on TEM grids, placed on filter paper, that retain the CRUD collected from the reactor fuel scraping process.

Additionally, samples may be prepared by placing a sample on a surface of a standard carbon support film for(S) TEM analysis that will dislodge a number of crystals from the surface layer of the flake, creating a mirror image of the CRUD surface of interest on the carbon paper with the crystals of interest captured on it.

As provided in FIG. 1, two main types of analysis are used to determine topographical, morphological and qualitative compositional information of each sample.

As provided in FIG. 1, samples are identified using SEM/EDXS (Scanning Electron Microscope/energy-dispersive X-ray spectrometry) characterization methodology 100, wherein a high resolution field emission scanning electron microscope multimode examination combines a high and low secondary electron detector and backscattered electron imaging. In an exemplary embodiment of the present invention, results of such an investigation are illustrated in FIGS. 2 to 5. Additionally, FIG. 6, as presented, illustrates comprehensive topographic, morphological and qualitative compositional information regarding the sample evaluated. Three-dimensional morphology is determined through using a multimode secondary electron imaging/lower electron imaging/backscattered electron imaging. This allows for determination of a relative presence and proportion of different phases and surface topography aggregation in the sample in macro scale, micro scale and nano scale, from 1.10 to 10 micron size following the left path of analysis as described in FIG. 1, down to 100 nanometer to 0.02 size if one follows the right path of analysis as described in FIG. 1.

Figure 6:
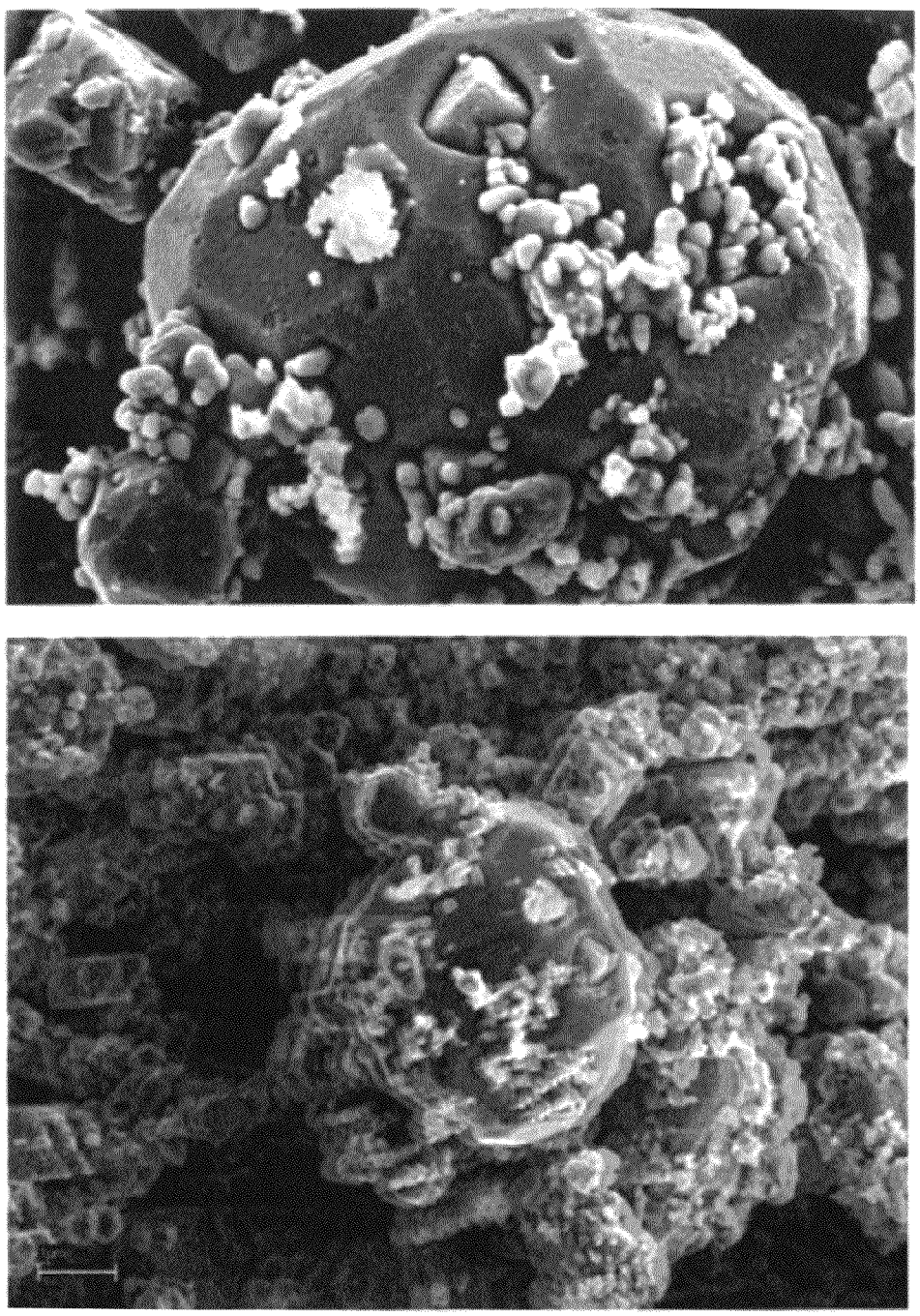
FIG. 6 is a High Resolution Field Emission SEM with mixed SE/BSE signal images of an uncoated BHC CRUD Flake.

In FIG. 6, various phases of a spinel structure found in a nuclear plant system are shown. Chemical composition of phases incorporated, as well as the composition of the spinel, can be obtained through energy-dispersive X-ray spectrometry. Results from all of the three-dimensional morphology, surface topography aggregation, flake shape/size 120 are obtained and recorded in a storage arrangement, such as a computer and compared to a structural/analytical data base 490.

To identify phase separation 150 according to the average atomic number, Z, multi-mode imaging is used to provide compositional information. The image intensity resulting from the multi-mode imaging is proportional to the average atomic number. In the present invention, multimode electron imaging is used to determine the compositional information of the sample by switching back and forth between secondary electron imaging, lower electron imaging, and backscattered electron imaging modes to eliminate the effect of charging specific to the radioactive field. By utilizing this type of imaging, this imaging has the ability to separate or mix secondary electron imaging, lower electron imaging, and backscattered electron imaging signals resulting in an improved control over the signal and resolution in the images. Multimode imaging using these various signals are illustrated in FIGS. 2 to 5 for the CRUD flake BHC sample at magnifications in the range of ×1000 to ×50,000.

In each of the FIGS. 2 through 5, the upper left quarter shows an upper secondary electron image (SEI). The lower left quarter shows a lower electron image (LEI) ($SE_1+SE_2$). The top right quarter shows a backscattered electron image as it provides compositional information to the image intensity proportional to the average atomic number, (Z). The lower right quarter is a backscattered electron image (labeled "topo" because the intensity reflects the sample topography). As described above, modes are switched during evaluation to eliminate charging concerns of the sample.

Figure 2:
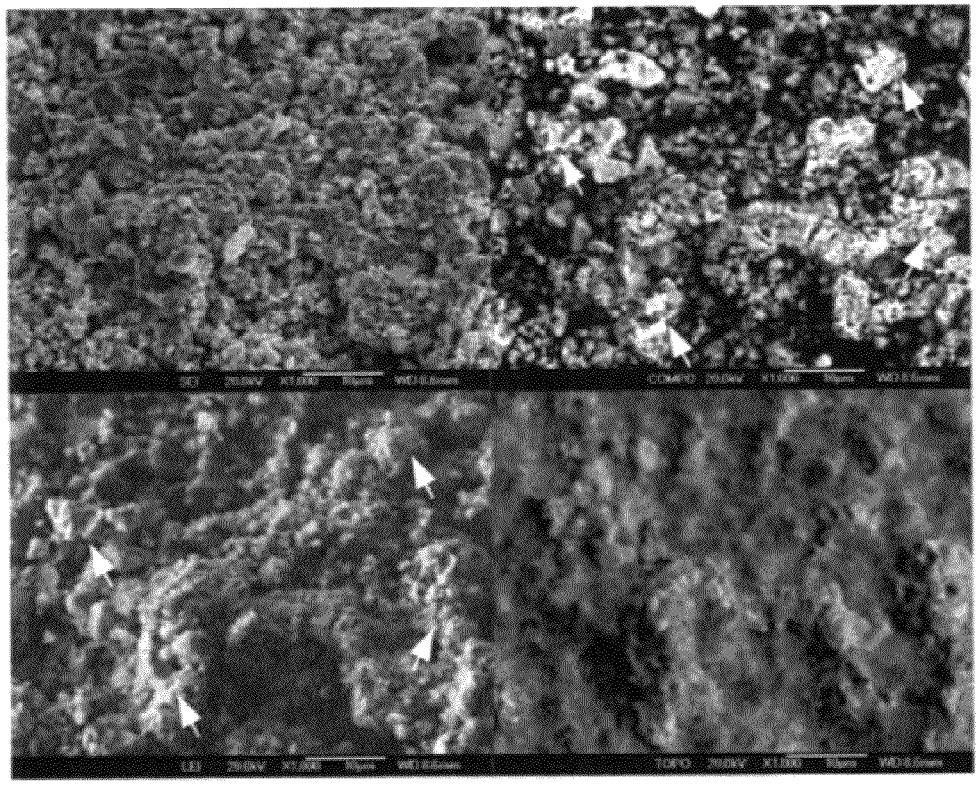
FIG. 2 is a 1,000× High Resolution SEM Multimode image of an uncoated CRUD flake sample.
Figure 3:
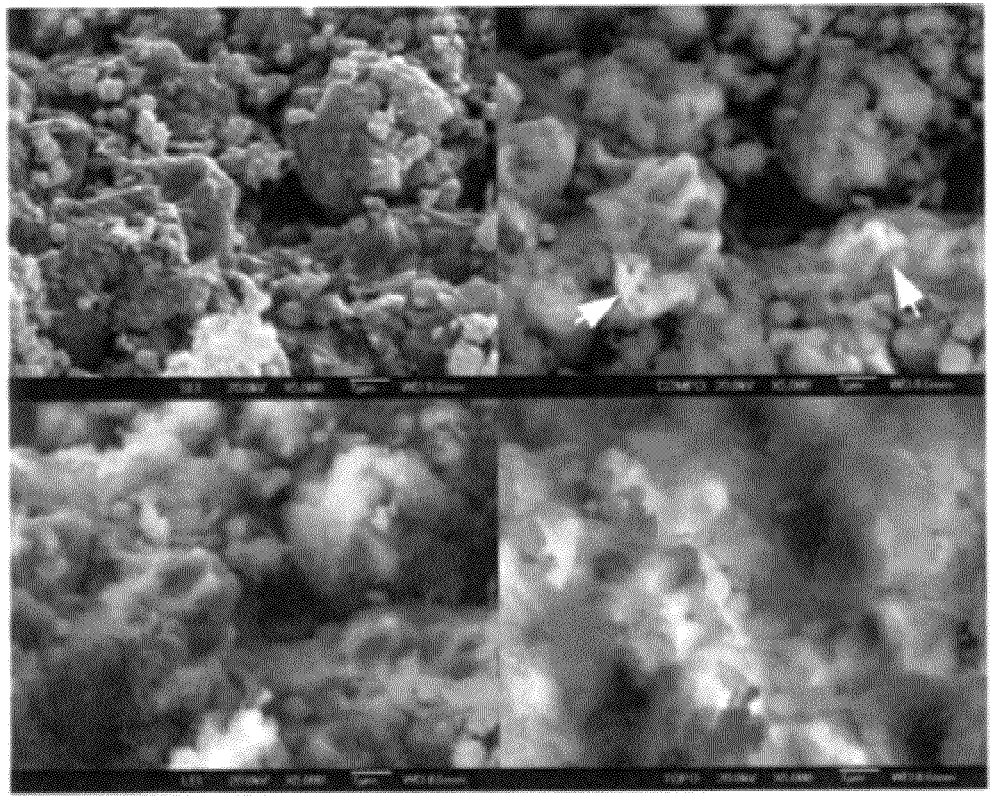
FIG. 3 is a 5,000× High Resolution SEM Multimode image of an uncoated CRUD flake sample.
Figure 4:
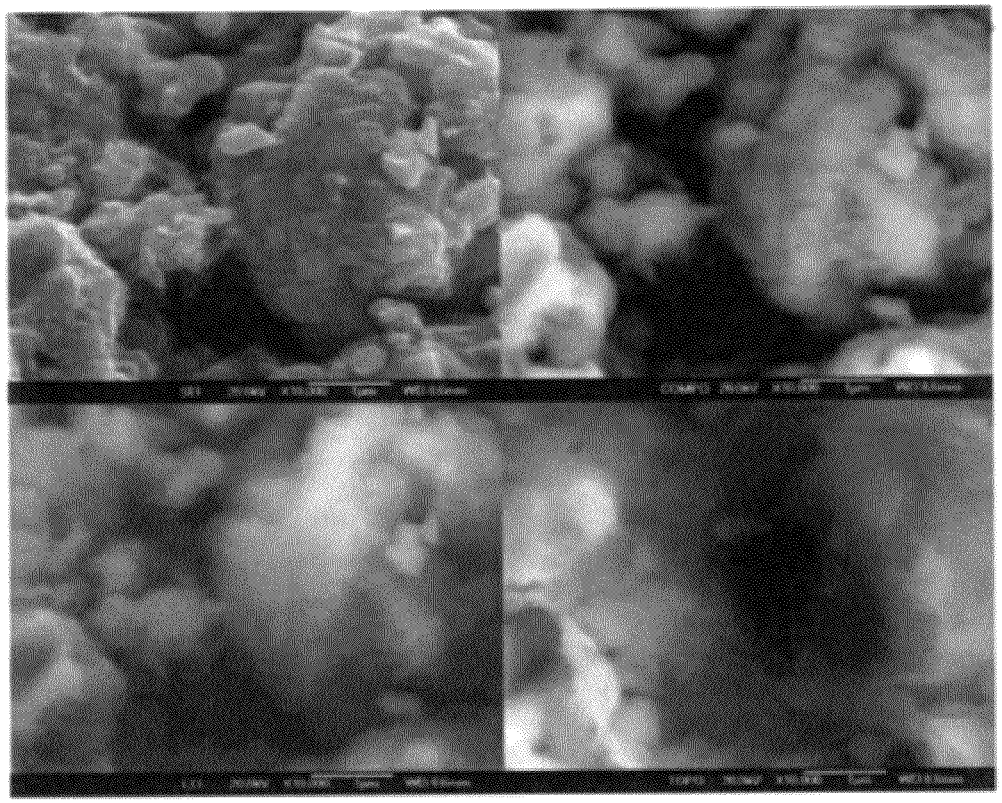
FIG. 4 is a 10,000× High Resolution SEM Multimode image of an uncoated CRUD flake sample.
Figure 5:
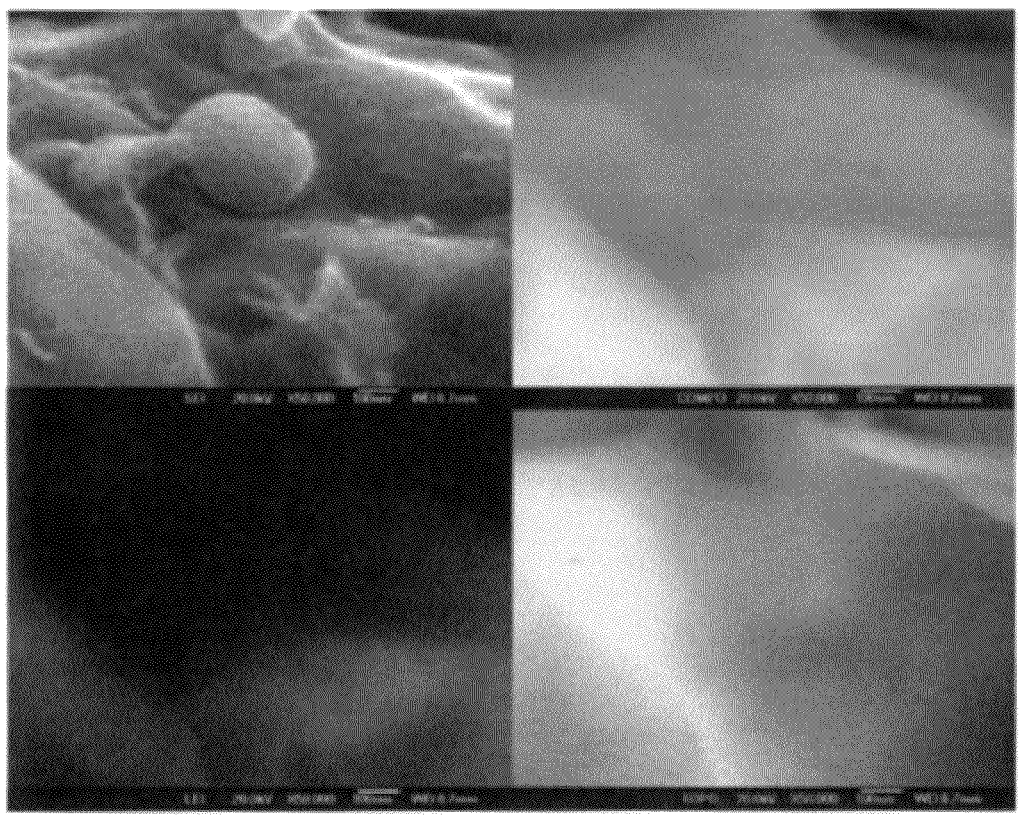
FIG. 5 is a 50,000× High Resolution SEM Multimode image of an uncoated CRUD flake sample.

Referring to FIG. 2, the backscattered electron image, top right quarter, reveals the location of higher atomic numbers or brighter faces on the sample surface. Lower atomic number materials have less bright surfaces for viewing. The secondary electron image, provided in the upper left quadrant, provides high resolution imaging of the surface morphology at all magnifications. The lower electron image, provided in the lower left quadrant, provides good resolution as well as compositional information or phase distinction at lower magnification. These images are less sensitive to surface charging because the backscattered electrons and secondary electrons are less dependent on surface charging. It is to be noted that as the image magnification increases, the topographical information image is increasingly different from the basic scanning electron microscope image.

As is provided in scanning electron microscopy, acceleration voltages of 20 to 30 kV are used for scanning electron microscope images in order to obtain high resolution of the signal in the image. Highly accelerated voltages, such as between 20 to 30 kV, are optimal for exciting characteristic X-rays in spot and elemental mapping and analysis. For radioactive deposits or in situations where charging is a problem, low-voltage scanning electron microscopy imaging reduces unwanted charging of the sample surface, greatly improving the imaging capability although signal strength is sacrificed for heavy elements.

Scanning electron microscopy is used for image captures (morphology and topography) of radioactive or heavily charged samples at low voltages (e.g. 0.5 to 5 kV) in secondary electron/backscattered electron mixing and energy and angle-selective backscattered electron detector filtering of secondary electron mode and at high voltage (20-30 kV) when obtaining chemical information in energy-dispersive X-ray spectrometry.

Figure 7:
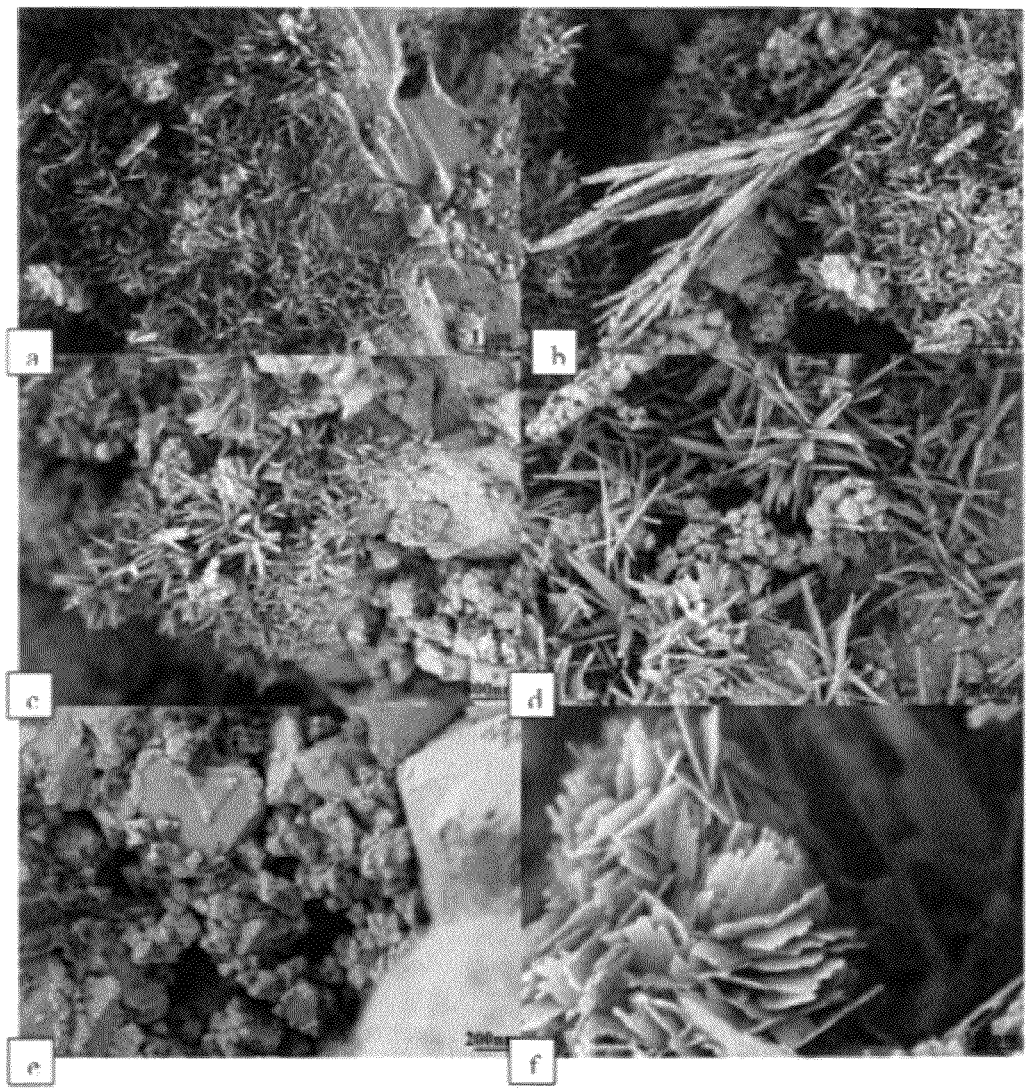
FIG. 7A is a High Resolution Low Voltage Field Emission SEM sampling at ×10,000 with an LEI image.
FIG. 7B is a High Resolution Low Voltage Field Emission SEM sampling at ×11,000 with an SEI image.
FIG. 7C is a High Resolution Low Voltage Field Emission SEM sampling at ×12,000 with an SEI/BSEI mixing.
FIG. 7D is a High Resolution Low Voltage Field Emission SEM sampling at ×30,000 with an SEI/BSEI mixing.
FIG. 7E is a High Resolution Low Voltage Field Emission SEM sampling at ×45,000.
FIG. 7F is a High Resolution Low Voltage Field Emission SEM sampling at ×100,000 with an SEI/BSEI missing and ExB filtering.

In order to illustrate the benefits of low voltage imaging, examples of high resolution field emission scanning electron microscope images taken using a low voltage of one kilovolt in selected areas of a CRUD flake are provided as illustrated in FIGS. 7B, 7C and 7D. Referring to FIGS. 7B, 7C and 7D, these images reveal several types of crystals with unusual morphologies, including a mixture of elongated 100 to 300 nm needlelike and thin plate shaped crystals sometimes forming characteristic crystalline "flowers", strands of twisted, long-beaded crystalline needles up to 8 nm in length and smaller sections of aggregated particles. These crystals are found in nuclear reactor heating surfaces.

Observation of the samples at magnifications of ×30,000 to ×100,000 reveal structural details of the hierarchical flake structures. Compact aggregated particles exhibiting a dense packing of 100 to 300 nm diameter grains with clearly visible boundaries and ultrafine precipitates 3 to 5 nm in diameter on their surfaces are visible near the center in FIG. 7D for example.

In the exemplary sample evaluated, agglomerated faceted tetrahedral and octahedral-shaped crystals show evidence of site-specific epitaxial-growth with crystalline nuclei of 20 to 50 nm in size as provided in FIG. 7E. Additionally, the thickness of thin plate shaped crystalline clusters was found to be 3 to 10 nm as provided in FIG. 7F.

The images provided demonstrate a resolution that is obtained on CRUD crystals at low voltages in field emission scanning electron microscopes. Secondary electron/backscattered electron mixing and energy and angle sensitive backscattered electron detector filtering of secondary electrons allow for this resolution of the image.

Figure 8A:
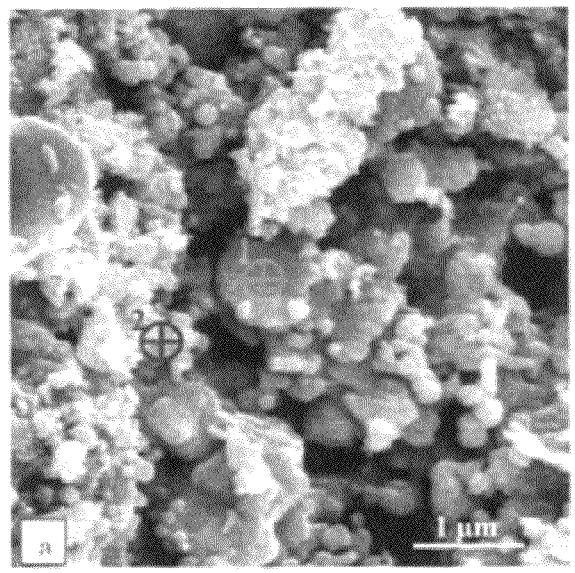
FIGS. 8A and 8B are High Resolution Field Emission SEM and "Spot" EDX spectra collected from two points of a BHC flake.
Figure 8B:
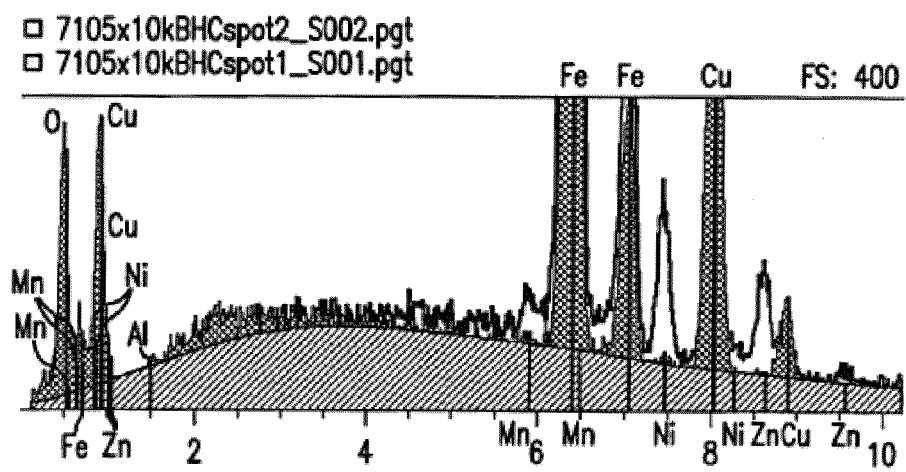

As provided in the methodology in FIG. 1, spot and elemental mapping analysis (EDXS imaging) is performed in step 150. Having determined the various crystal morphologies, the next step according to the present application is to obtain EDXS imaging from selected crystals to further identify the crystal's chemical composition. Selective site (or spot mode) analysis is performed under a multimode scanning electron microscope. This selective site analysis provides qualitative phase identification of the CRUD flake samples. As provided in FIG. 8A, a scanning electron microscope image of a BHC sample with locations of two spot analyses is provided as positions one (1) and two (2). Position one (1) is located on a relatively dark, micron sized particle while position two (2) is on an aggregate of smaller particles. The resulting EDXS spectra superimposed in FIG. 8B show distinct differences in the compositions of the two types of particles, with position two containing more iron as well as manganese, nickel and zinc. None of these components are present in appreciable amounts in position one. According to the present invention, for deposits presenting crystals of interest with sizes 3 μm and larger, multimode scanning electron microscopy/site-specific EDXS is an exemplary rapid analysis mode.

In quantitative EDXS analysis, the accuracy of quantification (from spot spectra and elemental maps) may be questionable if the spectra are not obtained from samples that are "polished" flat over a large area with a known geometry relative to the X-ray detector. This occurs because of poorly defined measurement conditions, and the occurrence of geometric mass and absorption effects on irregular sample surface effects.

To improve the interpretation and quantification of data obtained from irregular surfaces (unadulterated flake analysis surfaces) according to the present application, operating conditions for the microscope, such as the accelerating voltage, probe diameter, probe current, detector efficiency and acceptance angle, tilting angle, counting statistics, and sample related issues (such as the electrical and thermal conductivity, fluorescence induced by "hot" samples, sample stability under beam radiation, substrate material) are specified as part of the analysis.

Error may occur during quantification of EDXS data obtained from irregular surfaces based on standard-less atomic number-absorption fluorescence corrections (called ZAF correction), or X-ray depth distribution (called the Phi-Rho-Z, or PRZ). This error is due to poorly defined measurement conditions and/or the occurrence of a geometric mass effect, i.e. a defined measurement condition. Additionally the occurrence of the geometric mass effect (i.e. a variation in the emitted X-ray signal due to a complex surface topography and therefore the paths the X-rays encounter in reaching the detector) and absorption effects (mainly due to severe absorption of soft OK X-rays, that result in overestimation of the concentration of heavy metals) may occur.

In order to address error resolution, according to the present invention, a set of standard samples of interest for each specific deposit (e.g. $Fe_2O_3$, CuO, ZnO) has the EDXS data obtained for the samples under well defined conditions similar to deposits to be measured 170. If the sample is highly radioactive, the placement of standards for EDXS spectra will be on the grid in its immediate vicinity. This allows determination of the correction procedure that is necessary for accurate quantification of spot and elemental mapping analysis data from a particular scanning electron microscope in the same radioactive conditions. These procedures are applied to the EDXS spectra from unknown CRUD crystals to determine their compositions more quantitatively.

As samples will vary in configuration, geometric effects arising from the configuration must be taken into consideration. According to the present invention, a peak-to-background method is to be used to compensate for the effects on the analysis arising from the geometry of the sample. This method specifies that the characteristic X-ray peaks and continual background radiation produced in the same region of the sample are subject to the same absorption and backscatter conditions. Measurement of the peak-to-background ratio for the elements of interest can be compared with other elements in the sample as well as established standards, to determine if significant absorption and/or fluorescence are occurring. Such measurements are particular to each microscope and detector. If significant scattering is occurring from other parts of the sample, the method may be unreliable, since the measurement depends upon measuring the local background in the same area as the characteristic X-ray lines produced. If significant scattering occurs, a Monte Carlo simulation is used to assess the size of lateral errors. For complicated geometries, the approximation is only a general indication what parameters the microscope settings should be set at.

Figures 9A, 9B:
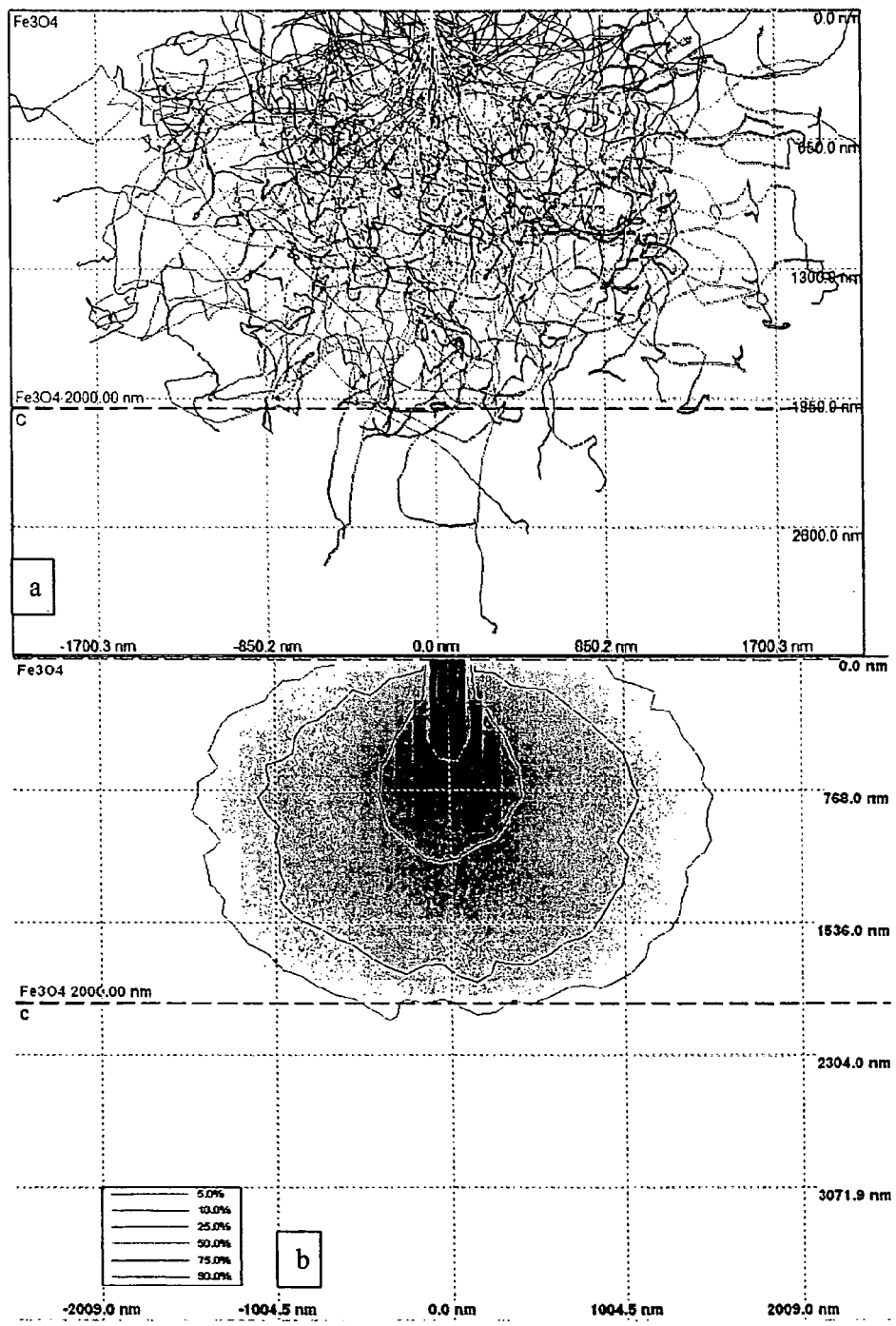
FIGS. 9 A, B and C are graphs and data of a Monte Carlo simulation of an interaction volume for a 2 μm thick $Fe_3O_4$ layer on a carbon substrate.
Figure 9C:
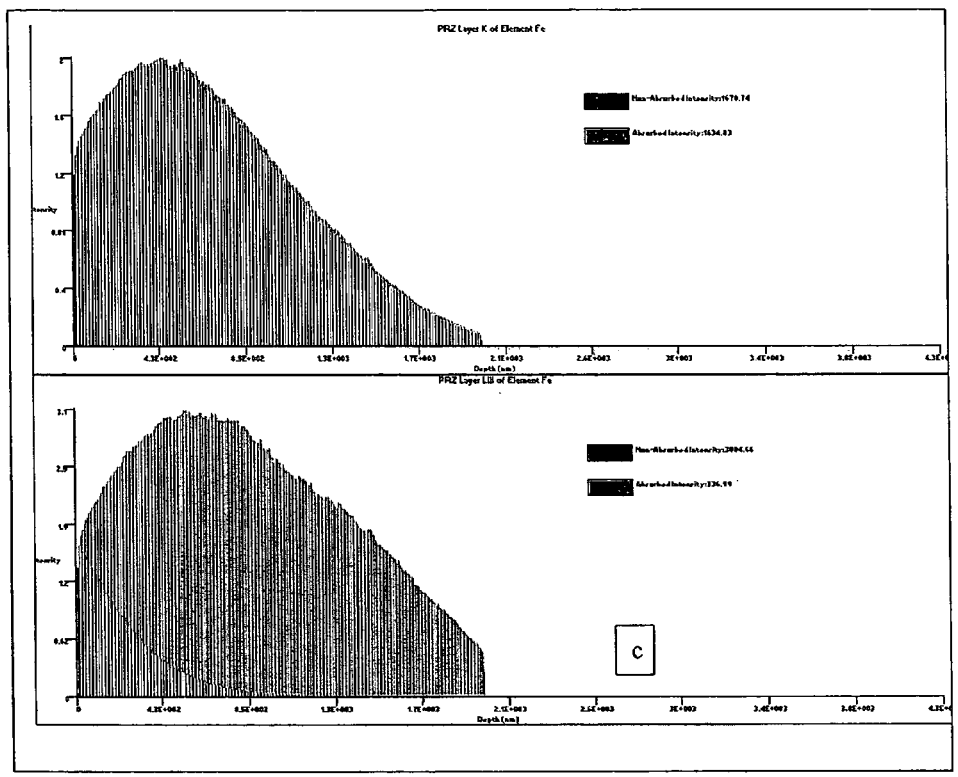

Monte Carlo simulations 500 are performed on the sample, as provided in FIGS. 9A and 9B, in order to assess the achievable lateral resolution expected during EDXS analysis from a particular material, and the effects of specific operating conditions, specimen thickness, density and chemical composition of the intensities of the emitted and absorbed X-rays as provided in FIG. 9C.

These exemplary embodiments provided by the Monte Carlo method provide an indication of expected behavior of the sample. These Monte Carlo simulations are used as a guide for optimizing the microscope conditions for particular types of specimens, rather than for quantitative comparisons with unknown specimens. A structural/analytical data base 490 may be used for storing and/or comparison of the above analysis.

In addition to the high resolution scanning electron microscope SEM/EDXS and site specific EDXS analysis performed, an alternative method step may be performed for analysis of samples. As provided in step 400, a scanning transmission electron microscope (S)TEM/SAED and EDXS using a conventional and high resolution imaging/electron diffraction and high spatial resolution is performed. In the methods provided in step 400, spot spectrum are used in addition to line scans, maps and spectrum imaging. As provided above, the utility of scanning electron microscope and EDXS is used for determining the morphology of the sample in question. Analytical transmission electron microscopy utilizing spot and elemental mapping analysis is highly complimentary to the scanning electron microscope methods and, in particular, enables a researcher to examine the internal structure of crystals 402, obtain EDXS analysis that are largely free from absorption and fluorescence effects/corrections 406, as well as providing electron diffraction information i.e. crystallographic information about the phases, such as their interplanar spacings and lattice type 404. Additionally, these analyses can be obtained from regions as small as 1 nm in diameter under optimal operating conditions. Thus, the spatial resolution for analytical transmission electron microscopy is an order to three orders of magnitude superior as compared to analytical field energy electrons (typically 200 kV) to pass through, or less than several hundred nanometers in thickness. Transmission electron microscopy is highly complementary to scanning electron microscopy, where the spatial resolution of spot and elemental mapping analysis is typically not better than 1000 nm.

Figure 10A:
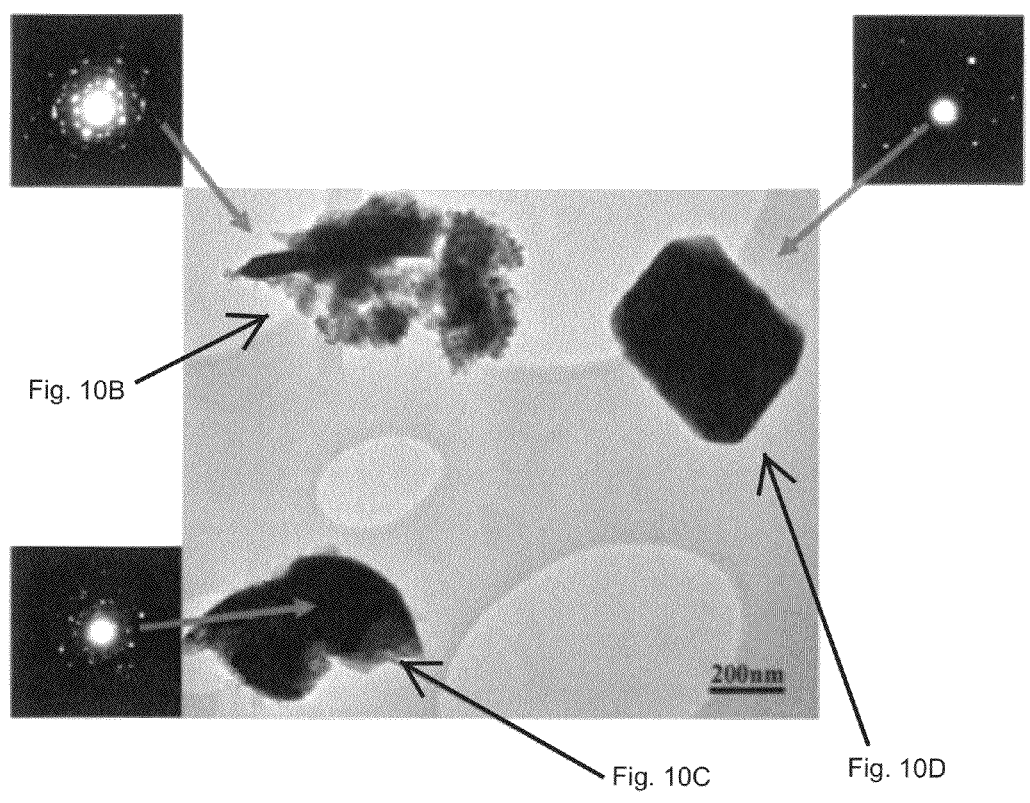
FIG. 10 is a BF-TEM/SAED and Spot EDX spectra from three particles released from BHC flake analyzed at 100,000×.

As provided in FIG. 10, a bright field (BF) transmission electron microscopy image of three CRUD particles suspended on a carbon film is illustrated. The crystals are selected from a sample and are indicated by arrows and have the same morphologies as typical submicron crystals, previously observed in a sample by scanning electron microscopy (e.g. a faceted oblique sheath (top right), a cluster of fine aggregates (top left) and irregular plates (bottom left). Consequently, these crystals are from nuclear reactor primary reactor system heating surfaces.

Selected-area electron diffraction (SAED) patterns obtained from each crystal are shown adjacent to the crystals in question. The crystal in the upper-right, displays a single-crystal spot pattern, while the other two phases display ring patterns. These ring patterns indicate that they are composed of many smaller nano-crystals.

To identify the phases, the d-spacings of the phases are determined from these SAED patterns and compared with d-spacings on file for various compounds in crystallographic databases.

Identification of the phases of the crystals is also facilitated by simultaneously determining their compositions 406, as indicated by the three EDX spectra in FIG. 10, again located immediately adjacent to each phase, or aggregate.

These EDX spectra accurately reflect the actual particle compositions because the geometric and absorption issues present in the SEM are largely mitigated in the TEM.

Examination of the three EDX spectra indicates that the faceted crystal in the top-right contains a large amount of Fe, Zn and Cu, as well as Ni, Mn and minor amounts of Al and Sn. This is in contrast to the particles in the top left, which contain mainly Fe, Cu and O, and the particles in the lower left, which contain Fe, Cu and O, but also substantial amounts of Al and Si.

In conclusion, FIG. 10 illustrates how the TEM procedure provides morphological 402, crystallographic 404 and compositional information 406 for submicron CRUD particles with unambiguous interpretation, different from SEM/EDXS characterization paths. Such analyses can be performed on larger crystals, but these would need to be isolated and thinned to electron transparency to do this. For the larger crystals, SEM/EDXS characterization paths may be more appropriate from an economical point of view.

Spectra may be compared between different measurement types.

Figure 11:
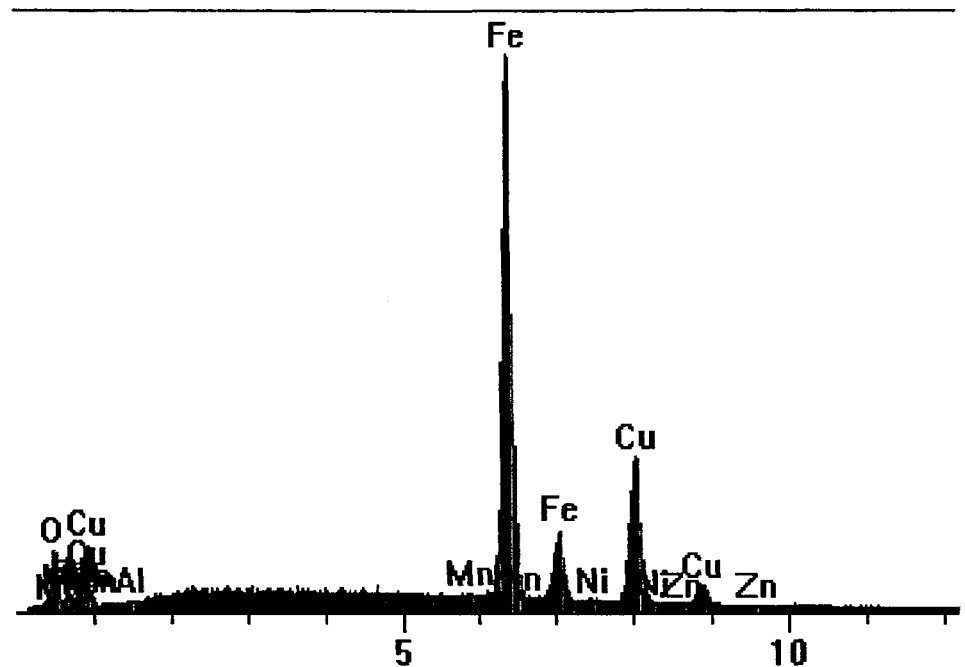
FIG. 11 is a high resolution field emission SEM spot EDX spectrum of aggregated BHC CRUD flake particles and standard-less quantification results based on a ZAF correction.

For example, comparison of spot EDX spectra from the BHC CRUD flake acquired in the field-emission SEM with an accelerating voltage of 20 kV (FIG. 11) with one acquired in the TEM at 200 kV (FIG. 12) shows that the peak-to-background ratio in the latter case is significantly higher. This ratio is higher due to an increase in the over-voltage, or the ratio between the accelerating voltage and the voltage necessary to excite characteristic X-rays in the specimen, by factor 10, from 20 to 200 kV. As a result, absorption of soft OK X-rays is significantly lower and the ratio of the peak intensities of Fe to O, i.e., FeK/OK, decreases from 13.32 to 2.71 from the SEM to the TEM. These data indicate that the oxygen concentration in the sample should be close to 57% as obtained from the TEM, as compared to 32.9% O as estimated by the ZAF-based standardless quantification procedure in the field-emission SEM, as indicated in the accompanying tables 1 and 2 as well as FIGS. 11 and 12. Note that the spectrum and tables as well as FIG. 12 were obtained from the particles visible in the bottom-left corner of FIG. 10. Similar conclusions concerning oxygen generated X-rays would apply to the spectra in FIG. 10.

Figure 13:
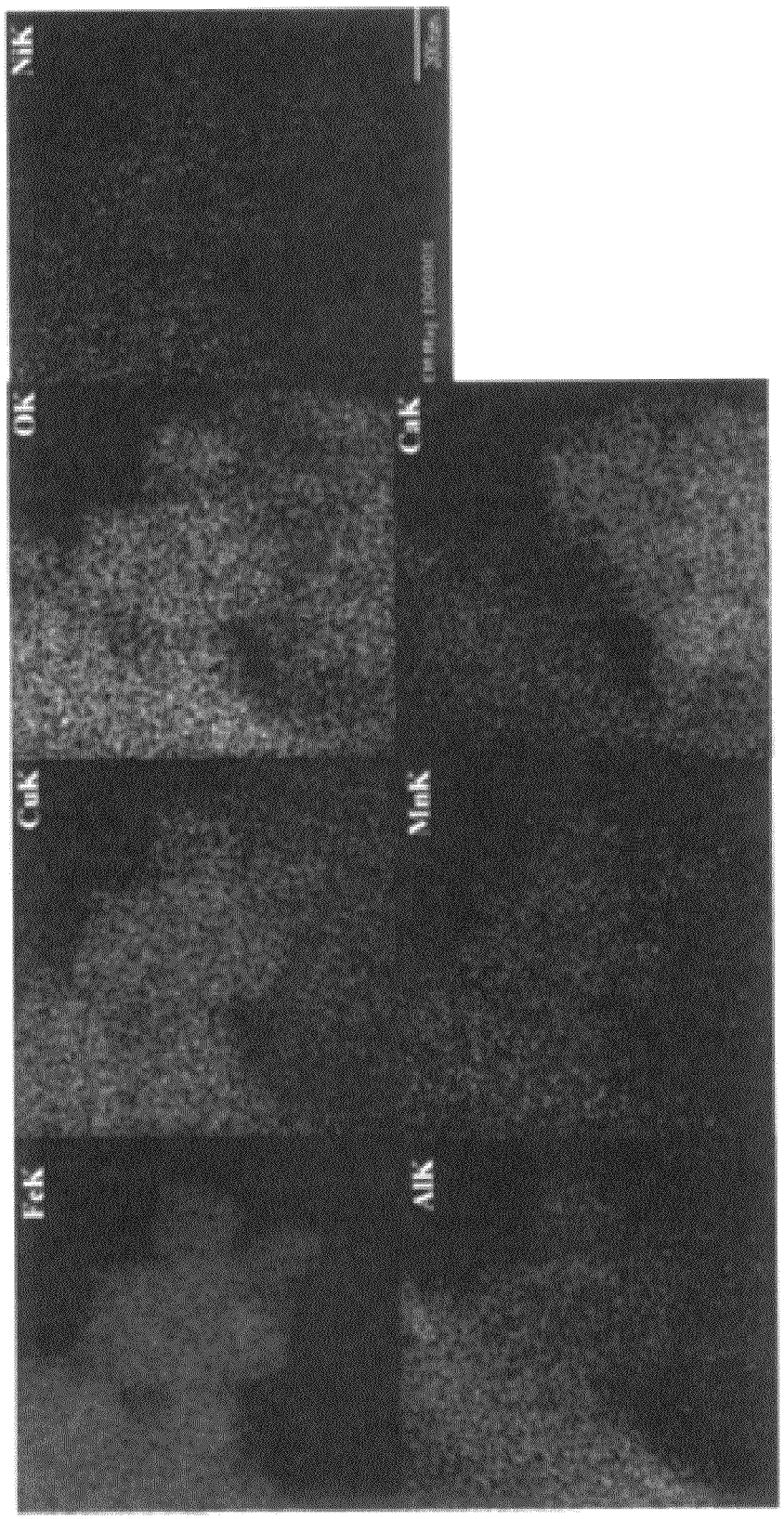
FIG. 13 is a digital X-ray elemental map using the Fe, K, CuK, OK, NiK, AlK, MnK and CaK peaks, acquired from a BHC CRUD flake.

As provided in FIG. 13, X-ray elemental maps acquired from the submicron sized CRUD flake particles are provided according to scanning transmission electron microscopy. This agglomerate of submicron sized particles is similar to that indicated as provided in position 2 in FIG. 8 as well as to the aggregates of similar submicron sized particles as provided in FIG. 7E.

Figure 12:
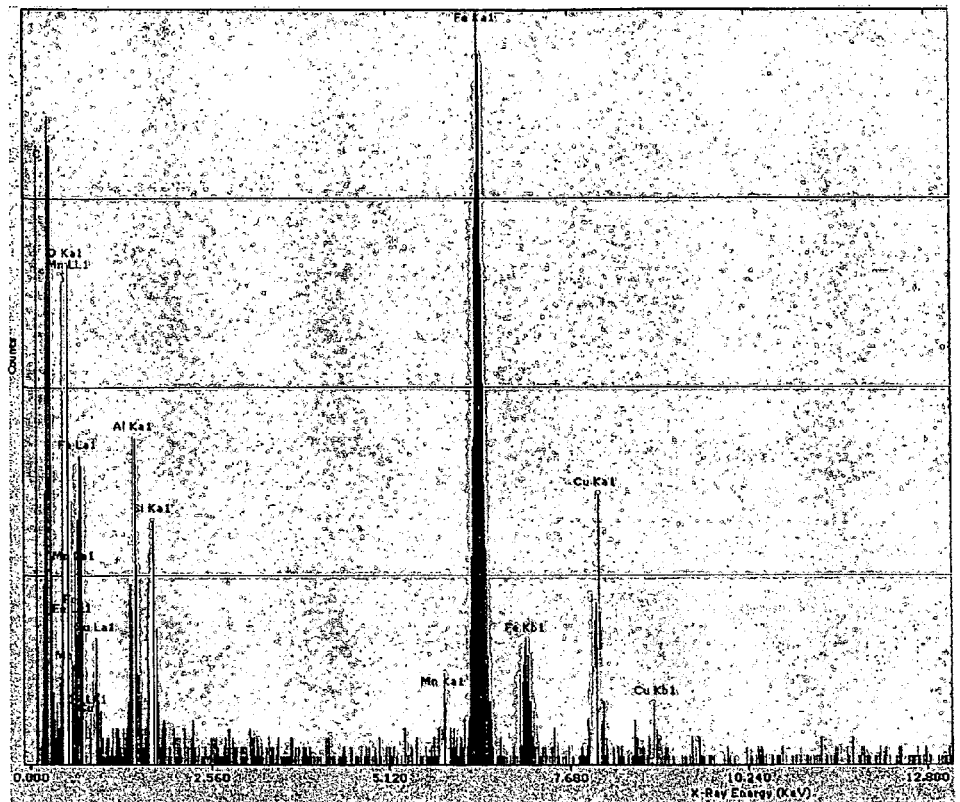
FIG. 12 is a spot EDX spectrum of an individual BHC flake particle and standard-less quantification results using a Cliff-Lorimer Thin-Film ratio method.

The distributions of the various elements in FIG. 12 demonstrate that there is a mixture of different phases in the agglomerate consisting of:

Fe—Cu—Ni—O  1)

Al—Mn—O, and  2)

Ca—O enriched particles.  3)

The Fe-rich phase (approximately 800 nm across) is evident extending from the top left corner and the FeK map, the Ca rich phase (400 to 600 nm in size) is present in the lower right region as evident from the CaK map and the AlMn containing phase (also approximately 800 nm in size in the maps) as is provided in the AlK and MnK maps.

Due to the higher accelerating voltage and thinness of the samples, X-ray mapping of the STEM enables researchers, in the present invention, to obtain a spatial resolution approaching 1 nm, which is nearly three orders of magnitude better than that of the analytical field emission scanning electron microscope. Additionally, researchers therefore have an increased sensitivity (at least by a factor of 10) to local variations in chemical composition and lesser of distortion of soft X-rays, as mentioned previously.

Referring to FIG. 13, a method step of elemental mapping in scanning transmission electron microscopy is performed to ascertain the distribution of phases in aggregates in the sample. This method step is complementary to obtaining quantitative analysis of particular areas, or phases, using the spot mode shown in the previous section. This applies to both scanning electron microscopy and scanning transmission electron microscopy at 20 kilovolts or 200 kilovolts respectively.

Chemical composition quantification standards 406 may also be used to aid in analysis of (S)TEM/SAED/EDXS data. Analytical Electron Microscopy Connection with Crystal Databases Data collected through scanning electron microscopy/EDXS 100 or (S)TEM/SAED/EDXS 400 are, as provided above in the present application, connected to crystallographic material phases using one or more of the pieces of information extracted from the analysis, such as morphological information 402, crystal lattice length 404. This allows for a rapid identification of a crystal structure. The results obtained from analysis are compared to a standard for ease of identification.

Results obtained are compared to the crystalline structures 410 found in the power diffraction file (PDF) crystal database from the International Center for Diffraction Data (ICDD) to determine the structures and morphologies of possible spinel, hematite and silicate crystals relating to the deposit for a number of 28 spectra are discussed below in an exemplary embodiment.

To date, the latest version of PDF database allows an end user to integrate data retrieval and data analysis, thus results from SEM and other methodologies provided above are compared to the database. All entries have been put into a relational database format. In this format, all the entry fields for diffraction, crystallographic, bibliographic, and physical property data are placed in individual tables.

In an exemplary embodiment, 28 energy-dispersive X-ray analysis from a radioactive deposit were examined to determine the most likely compound or compounds based on morphology, the elemental ratios and the information from the PDF Crystal database. The spot and elemental mapping and also spectra were acquired in the scanning electron microscope although several were obtained in the transmission electron microscope. The analysis results are provided in accompanying Table 1, with the result from the search of the PDF database. This table includes the spectrum identification (columns 1 and 8), the approximate compositions of the samples based on the standard-less spot and elemental mapping analysis (column 2), the identification of the sample (column 3), notable features associated with the crystals, either morphological or compositional (column 4), the likely compound type based on comparison of the compositional analysis with the PDF data (column 5), the metal/oxygen ratio obtained in the spot and elemental mapping analysis (column 6), and the iron/copper ratio in crystals containing these elements (column 7).

TABLE 1

Possible Compounds/Composition in Deposits According to PDF-4 File Selection

| File (All Kinds) | Composition (at. %) | Sample | Notable Features | Possible Compound(s)* (In order of possibility) | Metal/O | Fe/Cu | Spectrum # (lower-right-corner) |
|---|---|---|---|---|---|---|---|
| _S006.pgt (5) | Fe77Cu2Mn1O20 | NA-1 | Micron-size, needle-like clusters - high Fe | Fe3O4 variation | 80/20 | 77/2 | 1 |
| _S005.pgt (5) | Fe75Cu2Mn1O23 | NA-1 | Rod-like submicron agglomerate | Fe3O4 variation | 77/23 | 75/2 | 2 |

TABLE 1-continued

Possible Compounds/Composition in Deposits According to PDF-4 File Selection

| File (All Kinds) | Composition (at. %) | Sample | Notable Features | Possible Compound(s)* (In order of possibility) | Metal/O | Fe/Cu | Spectrum # (lower-right-corner) |
|---|---|---|---|---|---|---|---|
| _S001.pgt (5) | Fe74Cu4O23 | NA-1 | Sub-micron agglomerated particles | Fe3O4 variation | 77/23 | 74/4 | 3 |
| _S002.pgt (5) | Fe70Cu9Mn1O20 | NA-1 | Several-micron rods | Fe3O4 variation | 80/20 | 70/9 | 4 |
| _S007.pgt (5) | Fe69(Cu, Mn)1O31 (Cr)trace | NA-1 | Same, different location | Fe3O4 variation | 69/31 | 69/1 | 5 |
| _S004.pgt (5) | Fe64Cu3Mn1O33 | NA-1 | Clusters micron-size needles/laths | Fe3O4 variation | 67/33 | 64/3 | 6 |
| 1 | Fe43Cu3O54 | BHC | Fine aggregate (few plates) | Fe3O4 | 46/54 | 43/3 | 7 |
| _S002.pgt (2) | Fe87Cu3Ni1Mn1 (Al, Cr, Ti, Zn)1O8 | NA-1 | Flat particle, sub-micron | Fe3O4 variation | 92/8 | 87/3 | 8 |
| _S001.pgt (2) | Fe84Cu3Ni1Mn1O12 (Al, Zn)trace | NA-1 | Granular, sub-micron | Fe3O4 variation | 88/12 | 84/3 | 9 |
| _S003.pgt (5) | Fe64Cu2Zn4Mn1O29 (Ni)trace | NA-1 | Micron-size thick plate | (Zn, Mn, Fe)(Fe, Mn)2O4 | 71/29 | 64/2 | 10 |
| S001.pgt (1) | Fe64Cu10Zn3Ni3(Mn, Al)1O19 | BHC | Granular, micron-size | Fe3O4 variation | 81/19 | 64/10 | 11 |
| 2 | Fe32Cu4Zn15Al2(Mn, Ni, Sn)1O46 | BHC | Sub-micron faceted crystal - has Zn | Fe3O4, Fe2O3 | 54/46 (1.17) | 32/4 | 12 |
| 3 | Fe22Cu5Al8Si7Mn1O57 | BHC | Lath like - has Si | Fe3O4, Fe2O3 | 43/57 (0.75) | 22/5 | 13 |
| FIG. 14 | Same as TEM #3 above | | | Fe3O4, Fe2O3 | 43/57 (0.75) | 22/5 | |
| _S002.pgt (1) | Fe46Cu21O33 (Ni, Mn, Al)trace | BHC | Granular, sub-micron, low Fe/Cu | Fe2CuO4, Fe3O4, Fe2O3 | 57/33 (2) | 46/21 | 15 |
| FIG. 13 | Same as_S002.pgt (1) above | | High Cu, or low Fe/Cu ratio | Fe2CuO4, Fe3O4, Fe2O3 | 57/33 (2) | 46/21 | |
| _S004.pgt (2) | Fe75Cu19Zn4O2 | NA-1 | Highly faceted, micron-size | Fe2CuO4 variation | 98/2 | 75/19 | 16 |
| _S004.pgt (4) | Fe12Cu82O6 | BHC | Several-micron covered in granules and needles, high Cu | Cu + Cu2O, Cu2O, CuO | 94/6 | 12/82. | 17 |
| _S006.pgt (2) | Fe5Cu86O9 (Zn) trace | NA-1 | Same, different location - high Cu | Cu + Cu2O, Cu2O, CuO | 91/9 | 5/86. | 18 |
| _S001.pgt (2) | Fe20Cu58Zn2O21 (Ni, Mn) trace | NA-1 | Large, rough particle - high Cu | FeCu3Zn2O6.5, Cu2O, CuO | 79/21 | 20/58 | 19 |
| FIG. 10 | High Cu, low Fe | | | FeCu3Zn2O6.5, Cu2O, CuO | | | 20 |
| _S001.pgt (3) | Fe5Cu50Al25Zn10O11 | NA-1 | High Cu, Al, Zn | Cu2AlO4 | 89/11 | 5/50. | 21 |
| _S003.pgt (3) | Fe7Cu51Al24Zn8O9 | NA-1 | High Cu, Al, Zn | Cu2AlO4 | 91/9 | 7/51. | 22 |
| _S001.pgt (4) | Fe27Cu1Al32Zn18O23 | BHC | Several-micron particle, high Al, Zn | Fe2AlO4 or FeAlZnO4 variation | 77/23 | 27/1 | 23 |
| _S001.pgt (3) | Fe18Cu4Al29Zn37Ni1O11 | NA-1 | High Al, Zn | Al2ZnO4, Fe2CuO4 or FeAlZnO4 variation | 89/11 | 18/4 | 24 |
| _S002.pgt (4) | Ca33P20Fe6Cu1O41 | BHC | Highly faceted, several micron size | Ca3(PO4)2 | | | 25 |
| _S003.pgt (4) | Ca36P21Fe4Mn2O37 (Cu)trace | BHC | Same, different location | Ca3(PO4)2 | | | 26 |
| _S001.pgt (3) | C80Fe3Cu1Al4Zn7O5 | NA-1 | High C | Graphite? | | | 27 |
| _S001.pgt (3) | C79Fe1Cu10Al4Zn2O5 | NA-1 | Very small particle - high C | Graphite? | | | 28 |

*List of possible compounds on following page.

As is identified in Table 2, for the exemplary embodiment, most compounds appear to be some variation of $Fe_3O_4$ or similar spinel based structures with Cu, Mn, Al and Zn (and to a lesser extent occasional Ni, Cr, Ti), substituting for Fe, or one another. There are clearly Fe and Fe,Cu-based variations of this structure, e.g. spectra #1-11, as well as Cu, Al and Al, Zn variations, e.g. spectra #21-24.

TABLE 2

Spinel Compounds in Deposit Including Metal to Oxygen Ratio and Lattice Parameters

| *Compound | Metal/O ratio | Fe/Cu ratio | Fe3O4 or spinel variation | Lattice Parameters. a, b, c (nm) |
|---|---|---|---|---|
| FeO | 1 | | | 0.4312 |
| Fe2O3 | 0.67 | | | 0.834, 0.8322 |
| (Fe0.86 Al10.14)2O3 | 0.67 | | | 0.8391 |
| Fe3O4 | 0.75 | | Yes | 0.8391 |
| CuO | 1 | | | 0.5118, 0.3146, 0.4662 |
| Cu2O | 2 | | | 0.426 |
| CuMnO2 | 1 | | | 0.5898, 0.2884, 0.553 |

TABLE 2-continued

Spinel Compounds in Deposit Including Metal to Oxygen Ratio and Lattice Parameters

| *Compound | Metal/O ratio | Fe/Cu ratio | Fe3O4 or spinel variation | Lattice Parameters. a, b, c (nm) |
|---|---|---|---|---|
| Fe2CuO4 | 0.75 | 2 | Yes | 0.8216, 0.8216, 0.8709 |
| Fe2ZnO4 | 0.75 | | Yes | 0.8433 |
| Fe2AlO4 | 0.75 | | Yes | 0.8273 |
| Al2ZnO4 | 0.75 | | Yes | |
| Al2CuO4 | 0.75 | | Yes | 0.8079 |
| AlCuO2 | 0.75 | | | 0.2863, 0.2863, 1.1314 |
| Al4Cu2O7 | 0.86 | | | 0.809 |
| Fe2MnO4 | 0.75 | | Yes | |
| Fe2Cu0.5Zn0.5O4 Many variations in Cu/Zn | 0.75 | 4 | Yes | 0.8425 |
| Fe2Cu0.4Zn0.6O4 Many variations in Cu/Zn | | 5 | Yes | 0.8402-19 |
| Fe2Cu0.6Zn0.4O4 | 0.75 | 4 | Yes | |
| Al2Cu0.6Zn0.4O4 | 0.75 | | Yes | 0.839 |
| Fe1.9Cu0.1Ni0.65Zn0.35O4 | 0.75 | 5 | Yes | 0.8446 |
| FeCu3Zn2O6.5 | 0.75 | 3.33 | | 0.988, 0.988, 0.8066 |
| Fe1.2Zn0.6Cu0.4Cr0.8O4 | 0.75 | 19 | Yes | 0.9283 |
| Fe2.83Al18.39Cr0.78Mg7.77Si0.03Zn0.07O4 | 0.92 | 0.33 | | 0.8122 |
| (Zn, Mn, Fe)(Fe, Mn)2O4 | 0.75 | 3 | Yes | 0.8458 |
| CuFeMnO4 | 0.75 | 1 | Yes | 0.84 |
| CuAlMnO4 | 0.75 | | | 0.5805, 0.5805, 0.828 |
| Fe2Zn0.9Mn0.1O4 Many variations | 0.75 | | Yes | 0.8453 |
| Fe2Zn0.2Mn0.8O4 Many variations | 0.75 | | Yes | 0.8514 |
| (Zn0.799Fe0.172Al0.029)(Fe0.02Al1.969O4) Many variations | | | | 0.8101 |
| (Zn0.399Fe0.519Al0.082)(Fe0.079Al1.912O4) Many variations | | | | 0.8128 |
| (Fe0.914Si0.086)(Fe0.998, Si0.002)2O4 | 0.75 | | Yes | 0.8392 |
| FeSiO2 | 0.75 | | | |
| Fe3Al12(SiO4)3 | | | | 1.1546 |
| FeCO3 | | | | 0.4679, 0.4679, 1.5336 |
| Ca3(PO4)2 | | | | 0.536, 0.536, 0.7698 |

*PDF files for all compounds above included in same order.

Review of the compounds in Table 2 indicates that elements such as Cu, Fe, Mn, Al and Zn readily substitute for one another and these spinel based structures, consistent with the results above. Examination of the lattice parameters for $Fe_3O_4$ based crystals show a wide range of cubic compounds with any lattice parameter around 0.84 nm or is of the $Fe_3O_4$ phase. This indicates the ease with which these elements substitute for one another and therefore, the almost endless range of possible compositions of spinel-type faces that a composition may have. This makes unique identification based on standardless compositional analysis difficult.

What is claimed is:

1. A method to analyze crystals in a deposit on a surface of a nuclear generating station heating surface, comprising the steps of:

extracting a deposit from the surface of the nuclear generating station heating surface;

preparing a sample of material from the deposit for testing, wherein the sample of material is configured to examine at least one of said crystals in its environment within the deposit such that an as found state of the extracted deposit can be tested;

conducting at least one of a high resolution scanning electron microscope/energy dispersive X-ray spectrometry of the sample and a scanning transmission electron microscope/selected area electron diffraction/spot and elemental mapping analysis of the sample;

if high resolution scanning microscope/energy dispersive X-ray spectrometry is conducted, further comprising the steps of:

conducting at least one of three-dimensional morphology, surface topography aggregation and determination of flake size/shape, phase separation and chemical composition quantification after the high resolution scanning electron microscope/energy dispersive X-ray spectrometry of the sample;

performing a Monte Carlo simulation of electron beam-specimen interaction after the at least one of three-dimensional morphology, surface topography aggregation and determination of flake size/shape, phase separation and chemical composition quantification; and storing results of the Monte Carlo simulation and the at least one of the high resolution scanning electron microscope/energy dispersive X-ray spectrometry of the sample, the three-dimensional morphology, surface topography aggregation and determination of flake size/shape, phase separation and chemical composition quantification in a structural data base;

if high resolution scanning microscope/energy dispersive X-ray spectrometry is not conducted, further comprising the steps of:

conducting at least one of an internal structure, morphology and crystal size/shape determination, a crystallography investigation and a chemical composition investigation after the scanning transmission electron microscope/selected area electron diffraction/spot and elemental mapping analysis of the sample; and storing results of the at least one of the internal structure, morphology and crystal size/shape determination, crystallography investigation and the chemical composition investigation in a crystallographic data system.

2. The method according to claim 1, wherein the Monte Carlo simulation predicts an expected behavior of the sample under specific operating conditions.

3. The method according to claim 1, wherein the step of preparing the sample of material comprises one of:

collecting a CRUD deposit directly on TEM grids placed on filter paper and placing the deposit on standard carbon support film to dislodge a number of crystals from a surface of a flake of the deposit.

4. The method according to claim 1, wherein the step of conducting at least one of three-dimensional morphology, surface topography aggregation and determination of flake size/shape, phase separation and chemical composition quantification after the high resolution scanning electron microscope/energy dispersive X-ray spectrometry of the sample is performed by alternating between imaging modes to eliminate charging effects resulting from a radioactive field developed during analysis.

5. The method according to claim 1, wherein one of the three-dimensional morphology and the phase separation is determined through scanning electron microscope multimode imaging.

6. The method according to claim 1, wherein a peak to background method is used during the step of conducting at least one of a high resolution scanning electron microscope/energy dispersive X-ray spectrometry of the sample to compensate for geometric effects of the sample surface.

7. The method according to claim 1, wherein both a high resolution scanning electron microscope/energy dispersive X-ray spectrometry of the sample and a scanning transmission electron microscope/selected area electron diffraction/spot and elemental analysis of the sample are performed.

8. The method according to claim 1, wherein the high resolution scanning electron microscope/energy dispersive X-ray spectrometry is used to identify phase separation according to an average atomic number of the sample.

9. The method according to claim 1, wherein scanning electron microscopy/energy dispersive X-ray spectrometry is used at both a voltage between 0.2 to 5 kV for one of radioactive and charged samples, and at voltages between 20 to 50 kV when obtaining chemical information in the high resolution scanning electron microscope/energy dispersive S-ray spectrometry.

10. The method according to claim 1, wherein the energy dispersive X-ray spectrometry is performed with standards for radioactive samples.

11. The method according to claim 1, wherein a peak to background method is used during the scanning electron microscope/energy dispersive X-ray spectrometry of the sample to compensate for geometric effects of the deposit.

12. The method according to claim 1, further comprising:
conducting transmission electron microscopy of the sample.

13. The method according to claim 12, wherein a selected area electron diffraction is performed during the step of transmission electron microscopy to determine d-spacings of crystal phases of the sample.

14. The method according to claim 1, further comprising:
comparing the stored results of the one of high resolution scanning electron microscopy/energy dispersive X-ray spectrometry of the sample and the scanning transmission electron microscopy/selected area electron diffraction/spot and elemental mapping to a crystallographic materials phase data system.

15. The method according to claim 1, wherein both high resolution scanning electron microscope/energy dispersive X-ray spectrometry of the sample and scanning transmission electron microscope/selected area electron diffraction/spot and elemental mapping analysis of the sample are conducted, and wherein the method further comprises the steps of:
conducting at least one of an internal structure, morphology and crystal size/shape determination a crystallography investigation and a chemical composition investigation after the scanning transmission electron microscope/selected area electron diffraction/spot and elemental mapping analysis of the sample; and,
storing results of the at least one of the internal structure, morphology and crystal size/shape determination, crystallography investigation and the chemical composition investigation in a crystallographic data system.

* * * * *